United States Patent [19]

Barron et al.

[11] Patent Number: 4,650,668

[45] Date of Patent: Mar. 17, 1987

[54] COMPOSITION FOR RELIEVING TOOTHACHE PAIN AND OTHER FORMS OF INTENSE PAIN

[76] Inventors: Larry Barron; Susan C. Barron, both of 7 Hamilton Avenue, Winnipeg, Manitoba, Canada, R2Y 2G4

[21] Appl. No.: 685,080

[22] Filed: Dec. 21, 1984

[51] Int. Cl.$^4$ .................. A61L 9/04; A61K 31/65; A61K 31/435; A61K 31/34
[52] U.S. Cl. ...................... 424/44; 514/154; 514/277; 514/474; 514/561
[58] Field of Search ................ 424/44, 154; 514/474, 514/561, 277

[56] References Cited

U.S. PATENT DOCUMENTS 3,910,958 10/1975 Tsuchihashi et al. ............ 260/340.5
4,186,270 1/1980 Dowd et al. ......................... 562/496

Primary Examiner—Donald B. Moyer
Assistant Examiner—John W. Rollins, Jr.
Attorney, Agent, or Firm—Kenneth M. Garrett

[57] ABSTRACT

A treatment for temporary relief of pain wherein a single dose comprises the following: 4 grams calcium gluconate by injection, 1 gram Vitamin C (calcium ascorbate), 100 mg magnesium hydroxide, 50 mg Vitamin $B_6$ (pyridoxine hydrochloride), 1 gram pantothenic acid, effervescent solution.

5 Claims, No Drawings

COMPOSITION FOR RELIEVING TOOTHACHE PAIN AND OTHER FORMS OF INTENSE PAIN

This invention is a non-toxic, non-allergenic formula that can be used by medical doctors and dentists to alleviate (temporarily) intense tooth pain as well as other forms of intense pain.

There is only one effective formula that works internally to alleviate tooth pain, and that is a formula invented by Susan and Larry Barron who hold the patent rights in Canada (issued Dec. 11, 1984, No. 1179267). The formula is comprised of 2 grams of calcium gluconate, 500 mg of pantothenic acid, 50 mg of $B_6$ (pyridoxine hydrochloride), 100 mg of magnesium hydroxide, 1 gram of buffered Vitamin C. These ingredients are put into an effervescent solution and drunk. The tooth pain disappeared. The formula works by causing cellular relaxation to occur. Calcium assists nerve impulse transportation. With this amount of calcium in the formula, nerve and muscle excitability is greatly reduced, cell relaxation occurs, and therefore, tooth pain is alleviated.

This formula has now been improved upon by the original inventors by providing for speedier relief because the calcium gluconate is transported all at once into the blood stream and is therefore available to the cells to select this large quantity as needed. This new approach with subsequent changes to the formula provides for relief of tooth pain as well as temporary relief of pain caused by many other sources. This new formula rivals the opiates used as pain relievers. Only by injection can all the calcium gluconate be available to the cells instantly. Whereas the original formula had to be emptied from the stomach thereby not allowing the calcium to be available all at once, the improved formula allows the calcium to be available all at once. Following the injection of calcium gluconate, the subject drinks the effervescent part of the formula, thereby enhancing the effectiveness of the calcium in providing pain relief.

Severely ill patients, whether the pain is from the tooth or from other causes, can have upset stomachs and might not be able to swallow or ingest the original formula, when the upset stomach is caused by the intense pain. The improved formula overcomes this problem. Once the pain starts to subside due to the calcium gluconate injection directly into the veins, the patient waits a few minutes until the pain has subsided sufficiently to alleviate the stomach discomfort and is then able to drink the rest of the formula in the effervescent solution. Then maximum pain-alleviating benefits are derived and relief from pain is achieved.

The method of administering the formula would be: The medical doctor would inject by syringe 4 grams of calcium gluconate into the veins of the patient. Then the patient drinks the following ingredients within a few minutes (mixed in an effervescent solution): 1 to 2 grams of Vitamin C in calcium ascorbate form, 1 gram of pantothenic acid, 100 mg of magnesium hydroxide and, 50 mg of $B_6$ (pyridoxine hydrochloride), with sufficient sodium bicarbonate and citric acid added to cause an effervescent reaction in water. If the pain is still present, the formula is repeated with its accompanying injection.

The improved formula can now relieve most types of intense pain more quickly, yet with no side effects that prescription medications can cause. The range of amounts which can be used in the combination is stated as calcium gluconate in the range of 1 to 4 grams, pantothenic acid (calcium d-pantothenate) in the range of 1 to 4 grams, Vitamin C (calcium ascorbate) in the range of 500 mg to 4 grams, $B_6$ (pyridoxine hydrochloride) in the range of 50 to 100 mg, magnesium hydroxide in the range of 100 mg to 300 mg.

What is claimed is:

1. A method of alleviating pain, which comprises:
   (a) injecting a human host in need thereof with from 1 to 4 grams of calcium gluconate; and
   (b) simultaneously or subsequently orally administering to the human host a composition comprising from 1 to 4 grams of a substance selected from the group consisting of pantothenic acid and the calcium salt thereof, from 500 mg to 4 grams of Vitamin C, from 50 to 100 mg of Vitamin $B_6$ and from 100 to 300 mg of magnesium hydroxide.

2. A method according to claim 1, wherein said oral composition further includes sodium bicarbonate and citric acid in amounts sufficient to render the composition effervescent in water prior to administration.

3. A method of alleviating pain in a human host, which comprises:
   (a) injecting the host in need thereof with about 4 grams of calcium gluconate; and
   (b) orally administering to the host a composition comprising about 1 gram of pantothenic acid, about 1 gram of Vitamin C, about 50 mg of Vitamin $B_6$ and about 100 mg of magnesium hydroxide.

4. A method according to claim 3, wherein said oral composition further includes sodium bicarbonate and citric acid in amounts sufficient to render the composition effervescent in water prior to administration.

5. A method according to claim 3, wherein the effervescent composition is orally administered at a time immediately after the injection of calcium gluconate up to a few minutes after such injection.

* * * * *